(12) United States Patent
Jaeschke et al.

(10) Patent No.: US 9,682,959 B2
(45) Date of Patent: Jun. 20, 2017

(54) ETHYNYL DERIVATIVES

(71) Applicant: Hoffmann-La Roche Inc., Little Falls, NJ (US)

(72) Inventors: Georg Jaeschke, Basel (CH); Lothar Lindemann, Basel (CH); Rainer E. Martin, Basel (CH); Antonio Ricci, Biel-Benken (CH); Daniel Rueher, Raedersdorf (FR); Heinz Stadler, Aadorf (CH); Eric Vieira, Frenkendorf (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/991,748

(22) Filed: Jan. 8, 2016

(65) Prior Publication Data

US 2016/0130255 A1     May 12, 2016

Related U.S. Application Data

(63) Continuation of application No. PCT/EP2014/064272, filed on Jul. 4, 2014.

(30) Foreign Application Priority Data

Jul. 8, 2013 (EP) ..................................... 13175535

(51) Int. Cl.
    *C07D 401/04*      (2006.01)
    *C07D 403/04*      (2006.01)

(52) U.S. Cl.
    CPC ......... *C07D 403/04* (2013.01); *C07D 401/04* (2013.01)

(58) Field of Classification Search
    CPC ..................................................... C07D 401/04
    USPC ........................................ 546/274.1; 514/341
    See application file for complete search history.

(56) References Cited

U.S. PATENT DOCUMENTS 8,648,088 B2 *    2/2014    Jaeschke .............. C07D 401/04
                                                                                                                                           514/275
2011/0251169 A1    10/2011    Green et al.

FOREIGN PATENT DOCUMENTS

| TW | 201136924 A1 | 1/2011 |
| WO | 2004/080998 A1 | 9/2004 |
| WO | 2011/128279 A1 | 10/2011 |

OTHER PUBLICATIONS

Written Opinion of ISR for PCT/EP2014/064272.

* cited by examiner

*Primary Examiner* — Patricia L Morris
(74) *Attorney, Agent, or Firm* — Tamara A. Kale

(57) ABSTRACT

The present invention relates to ethynyl derivatives as metabotropic glutamate receptor antagonists (negative allosteric modulators) for use in the treatment of, e.g., anxiety and pain, depression, Fragile-X syndrome, autism spectrum disorders, Parkinson's disease, and gastroesophageal reflux disease (GERD).

3 Claims, No Drawings

ETHYNYL DERIVATIVES

This application is a continuation of International Application PCT/EP2014/064272, filed Jul. 4, 2014, which claims the benefit of priority to European Application 13175535.7, filed Jul. 8, 2013, each of which is incorporated herein by reference in its entirety.

The present invention relates to ethynyl derivatives of formula I

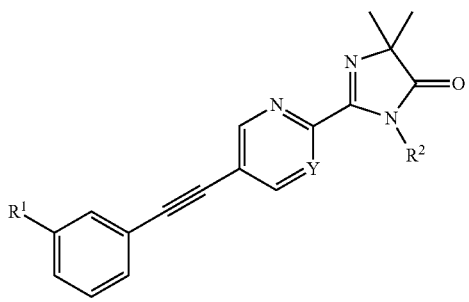

wherein
Y is N or CH;
$R^1$ is hydrogen, fluoro or chloro; and
$R^2$ is hydrogen or lower alkyl;
or to a pharmaceutically acceptable acid addition salt thereof.

It has now surprisingly been found that the compounds of general formula I are metabotropic glutamate receptor antagonists (NAM=negative allosteric modulators). Compounds with a similar main core have been generically described as positive allosteric modulators of the mGluR5 receptor. Surprisingly, it has been found that highly potent mGluR5 antagonists were obtained instead of mGluR5 positive allosteric modulators, which have a completely opposite pharmacology if compared with positive allosteric modulators.

An mGluR5 positive allosteric modulator (PAM) leads to increased receptor activity ($Ca^{2+}$ mobilization) in presence of a fixed concentration of glutamate, whereas an allosteric antagonist (negative allosteric modulator, NAM) leads to a reduction of receptor activation.

Compounds of formula I are distinguished by having valuable therapeutic properties. They can be used in the treatment or prevention of mGluR5 receptor mediated disorders.

In the central nervous system (CNS) the transmission of stimuli takes place by the interaction of a neurotransmitter, which is sent out by a neuron, with a neuro-receptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:
mGluR1 and mGluR5 belong to group I, mGluR2 and mGluR3 belong to group II and mGluR4, mGluR6, mGluR7 and mGluR8 belong to group III.

Negative allosteric modulators of metabotropic glutamate receptors, belonging to the first group, can be used for the treatment or prevention of acute and/or chronic neurological disorders such as Parkinson's disease, Fragile-X syndrome, autistic disorders, cognitive disorders and memory deficits, as well as chronic and acute pain and gastro-esophageal reflux disease (GERD).

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

Selective mGluR5 antagonists are especially useful for the treatment of disorders where reduction of mGluR5 receptor activation is desired, such as anxiety and pain, depression, Fragile-X syndrome, autism spectrum disorders, Parkinson's disease, and gastro esophageal reflux disease (GERD).

Objects of the present invention are compounds of formula I and their pharmaceutically acceptable salts, the above-mentioned compounds as pharmaceutically active substances and their production. Further objects of the invention are medicaments based on a compound in accordance with the invention and their manufacture as well as the use of the compounds in the control or prevention of mGluR5 receptor (NAM) mediated disorders, which are anxiety and pain, depression, Fragile-X syndrome, autism spectrum disorders, Parkinson's disease, and gastro-esophageal reflux disease (GERD, and, respectively, for the production of corresponding medicaments.

One embodiment of the present invention are compounds of formula I, wherein Y is N and $R^1$ and $R^2$ are as described above, for example the following compounds:
2-[5-[2-(3-Chlorophenyl)ethynyl]-2-pyrimidyl]-3,5,5-trimethyl-imidazol-4-one
3,5,5-Trimethyl-2-[5-(2-phenylethynyl)-2-pyrimidyl]imidazol-4-one or
2-[5-[2-(3-Fluorophenyl)ethynyl]-2-pyrimidyl]-3,5,5-trimethyl-imidazol-4-one.

One further embodiment of the present invention are compounds of formula I, wherein Y is CH and $R^1$ and $R^2$ are as described above, for example the following compounds:
2-[5-[2-(3-Fluorophenyl)ethynyl]-2-pyridyl]-3,5,5-trimethyl-imidazol-4-one
3,5,5-Trimethyl-2-[5-(2-phenylethynyl)-2-pyridyl]imidazol-4-one or
2-[5-[2-(3-Chlorophenyl)ethynyl]-2-pyridyl]-3,5,5-trimethyl-imidazol-4-one.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by processes described below, which process comprises a) reacting a compound of formula

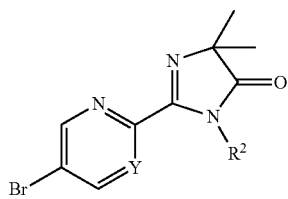

5 with a compound of formula

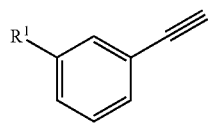

6 to a compound of formula

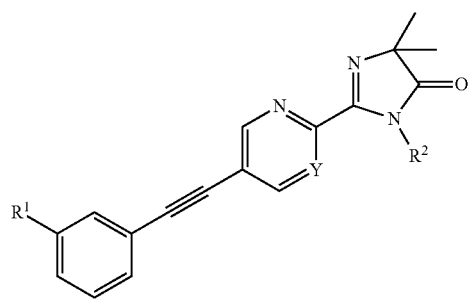

I wherein the substituents are as described above, or b) cyclizing a compound of formula

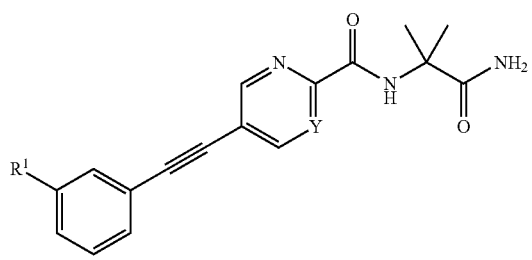

9 to a compound of formula

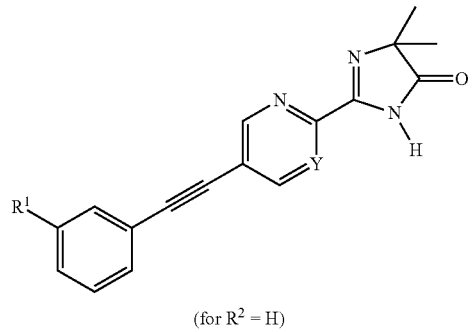

I (for R² = H)

and, if desired, alkylating the compound obtained to a compound of formula

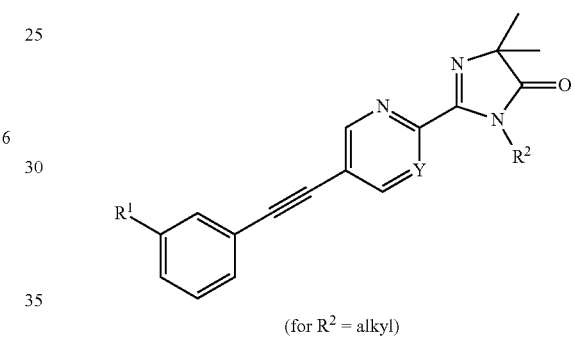

I (for R² = alkyl)

wherein the substituents are as described above.

The preparation of compounds of formula I is further described in more detail in schemes 1 and 2, and in examples 1-6.

Scheme 1

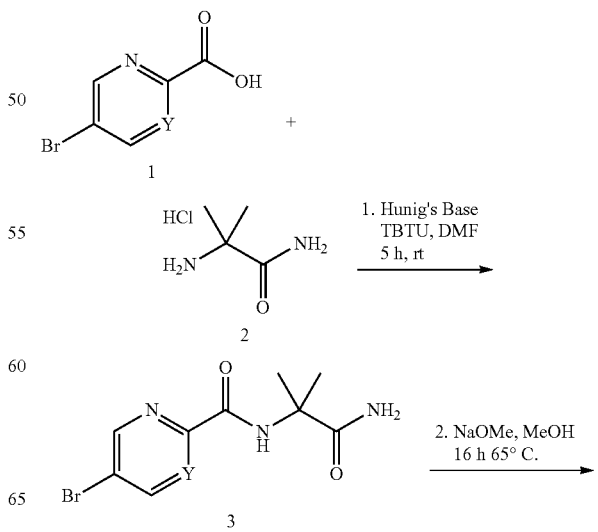

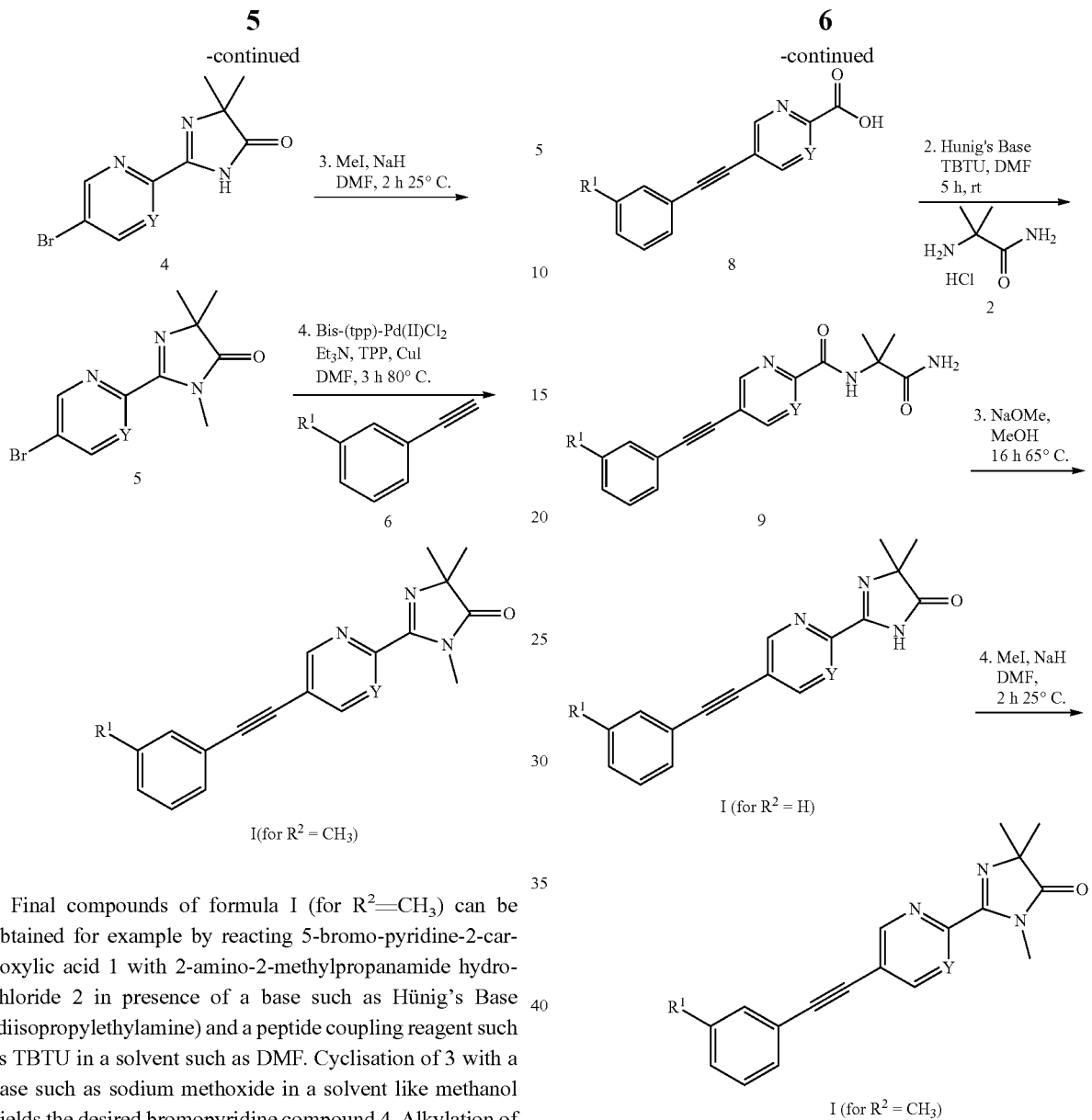

Final compounds of formula I (for R²=CH₃) can be obtained for example by reacting 5-bromo-pyridine-2-carboxylic acid 1 with 2-amino-2-methylpropanamide hydrochloride 2 in presence of a base such as Hünig's Base (diisopropylethylamine) and a peptide coupling reagent such as TBTU in a solvent such as DMF. Cyclisation of 3 with a base such as sodium methoxide in a solvent like methanol yields the desired bromopyridine compound 4. Alkylation of the bromopyridine compound 4 with an alkylating agent such as iodomethane in presence of sodium hydride in a solvent such as DMF yields the desired alkylated compound 5. Sonogashira coupling of 5 with an arylacetylene derivative 6 yields the desired final compounds of formula I (for R²=CH₃).

Scheme 2

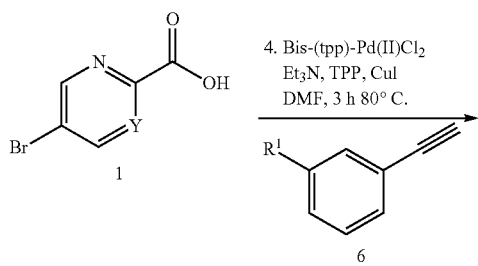

The compounds of formula I (for R²=CH₃) can also be obtained for example by Sonogashira coupling of 5-bromo-pyrimidine-2-carboxylic acid 1 with a corresponding arylacetylene derivative 6 to yield the desired acetylene carboxylic acid 8. Reacting 8 with 2-amino-2-methylpropanamide hydrochloride 2 in presence of a base such as Hunig's Base and a peptide coupling reagent such as TBTU in a solvent such as DMF yields the corresponding compound 9. Cyclisation of 9 in presence of a base such as sodium methoxide in a solvent like methanol yields the desired acetylene derivative I (for R²=H). Alkylation of compound I with an alkylating agent such as iodo-methane in presence of sodium hydride in a solvent such as DMF yields the desired final compounds of formula I (for R²=CH₃).

The invention also relates to the use of a compound in accordance with the present invention as well as its pharmaceutically acceptable salt for the manufacture of medicaments for the treatment and prevention of mGluR5 receptor mediated disorders as outlined above.

Pharmaceutically acceptable salts of compounds of formula I can be manufactured readily according to methods known per se and taking into consideration the nature of the compound to be converted into a salt. Inorganic or organic acids such as, for example, hydrochloric acid, hydro-bromic acid, sulphuric acid, nitric acid, phosphoric acid or citric acid, formic acid, fumaric acid, maleic acid, acetic acid, succinic acid, tartaric acid, methane sulphonic acid, p-toluene sulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

Moreover, the invention relates also medicaments containing one or more compounds of the present invention and pharmaceutically acceptable excipients for the treatment and prevention of mGluR5 receptor mediated disorders, such as anxiety and pain, depression, Fragile-X syndrome, autism spectrum disorders, Parkinson's disease, and gastroesophageal reflux disease (GERD).

The pharmacological activity of the compounds was tested using the following method: cDNA encoding rat mGlu 5a receptor was transiently transfected into EBNA cells using a procedure described by E.-J. Schlaeger and K. Christensen (*Cytotechnology* 1998, 15, 1-13). [Ca$^{2+}$]i measurements were performed on mGlu 5a transfected EBNA cells after incubation of the cells with Fluo 3-AM (obtainable by FLUKA, 0.5 µM final concentration) for 1 hour at 37° C. followed by 4 washes with assay buffer (DMEM supplemented with Hank's salt and 20 mM HEPES. [Ca$^{2+}$]i measurements were done using a fluorometric imaging plate reader (FLIPR, Molecular Devices Corporation, La Jolla, Calif., USA). When compounds were evaluated as antagonists they were tested against 10 µM glutamate as agonist.

The inhibition (antagonists) curves were fitted with a four parameter logistic equation giving IC$_{50}$, and Hill coefficient using the iterative non linear curve fitting software Origin (Microcal Software Inc., Northampton, Mass., USA).

The Ki values of the compounds tested are given. The Ki value is defined by the following formula:

$$K_i = \frac{IC_{50}}{1 + \frac{[L]}{EC_{50}}}$$

in which the IC$_{50}$ values are those concentrations of the compounds tested in µM by which 50% of the effect of compounds are antagonized. [L] is the concentration and the EC$_{50}$ value is the concentration of the compounds in µM which brings about 50% stimulation.

The compounds of the present invention are mGluR5 receptor antagonists. The activities of compounds of formula I as measured in the assay described above and as presented in the table hereafter are in the range of K$_i$<300 nM.

| Ex. | Structure | Name | Ki (nM) MPEP binding |
|---|---|---|---|
| 1 | 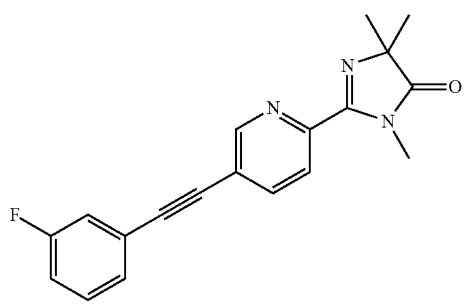 | 2-[5-[2-(3-Fluorophenyl)ethynyl]-2-pyridyl]-3,5,5-trimethyl-imidazol-4-one | 18 |
| 2 | 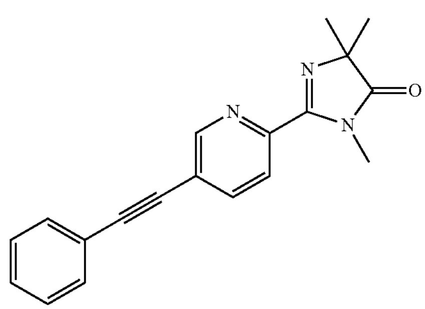 | 3,5,5-Trimethyl-2-[5-(2-phenylethynyl)-2-pyridyl]imidazol-4-one | 38 |

-continued

| Ex. | Structure | Name | Ki (nM) MPEP binding |
|---|---|---|---|
| 3 | 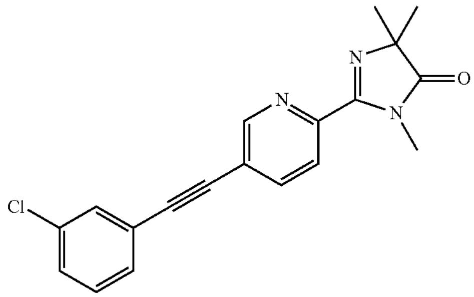 [SMILES: CN1C(=O)C(C)(C)N=C1c1ccc(C#Cc2cccc(Cl)c2)cn1] | 2-[5-[2-(3-Chlorophenyl)ethynyl]-2-pyridyl]-3,5,5-trimethyl-imidazol-4-one | 16 |
| 4 | 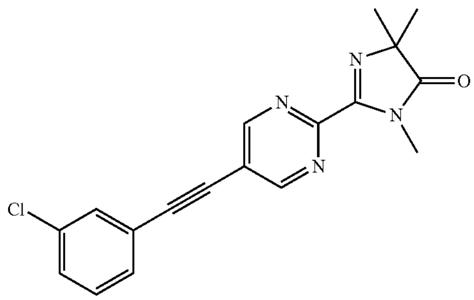 | 2-[5-[2-(3-Chlorophenyl)ethynyl]-2-pyrimidyl]-3,5,5-trimethyl-imidazol-4-one | 80 |
| 5 | 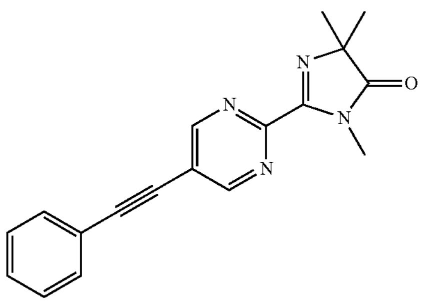 [SMILES: CN1C(=O)C(C)(C)N=C1c1ncc(C#Cc2ccccc2)cn1] | 3,5,5-Trimethyl-2-[5-(2-phenylethynyl)-2-pyrimidyl]imidazol-4-one | 281 |
| 6 | 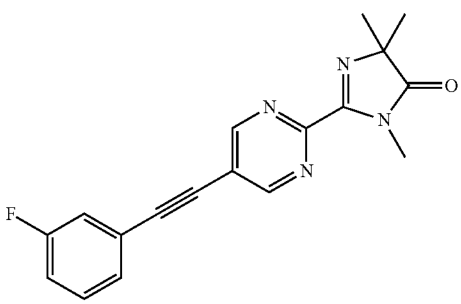 | 2-[5-[2-(3-Fluorophenyl)ethynyl]-2-pyrimidyl]-3,5,5-trimethyl-imidazol-4-one | 280 |

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention Tablets of the following composition are produced in a conventional manner:

|  | mg/Tablet |
| --- | --- |
| Active ingredient | 100 |
| Powdered. Lactose | 95 |
| White corn starch | 35 |
| Polyvinylpyrrolidone | 8 |
| Na carboxy-methyl starch | 10 |
| Magnesium stearate | 2 |
| Tablet weight | 250 |

The following examples are provided to further elucidate the invention:

EXAMPLE 1

2-[5-[2-(3-Fluorophenyl)ethynyl]-2-pyridyl]-3,5,5-trimethyl-imidazol-4-one

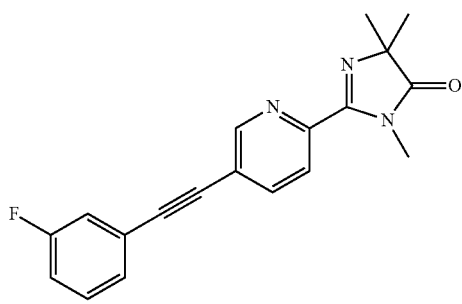 [SMILES: CN1C(=O)C(C)(C)N=C1c1ccc(C#Cc2cccc(F)c2)cn1]

Step 1: N-(2-Amino-1,1-dimethyl-2-oxo-ethyl)-5-bromo-pyridine-2-carboxamide

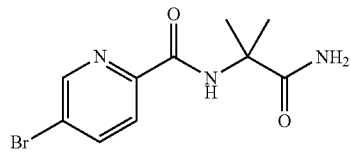 [SMILES: CC(C)(NC(=O)c1ccc(Br)cn1)C(N)=O]

5-Bromopicolinic acid (1 g, 4.95 mmol) was dissolved in DMF (10 ml) and Hünig's Base (2.59 ml, 14.9 mmol, 3 equiv.), TBTU (1.75 g, 5.45 mmol, 1.1 equiv.) and 2-amino-2-methylpropanamide hydrochloride (755 mg, 5.45 mmol, 1.1 equiv.) were added at room temperature. The mixture was stirred for 5 hours at room temperature. The reaction mixture was extracted with saturated NaHCO$_3$ solution and two times with ethyl acetate. The organic layers were extracted with water, dried over sodium sulfate and evaporated to dryness. The crude product was purified by flash chromatography on a 50 g silica gel column and eluting with an 0:100 to 100:0 ethyl acetate:heptane gradient. The desired N-(2-amino-1,1-dimethyl-2-oxo-ethyl)-5-bromo-pyridine-2-carboxamide (1.1 g, 78% yield) was obtained as a white solid, MS: m/e=286.3/288.3 (M+H$^+$).

Step 2: 2-(5-Bromo-2-pyridyl)-4,4-dimethyl-1H-imidazol-5-one

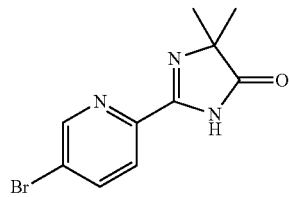

(1 g, 3.49 mmol) N-(2-Amino-1,1-dimethyl-2-oxo-ethyl)-5-bromo-pyridine-2-carboxamide (Example 1, step 1) was dissolved in methanol (20 ml) and a 5.4M solution of sodium methoxide in methanol (6.47 ml, 34.9 mmol, 10 equiv.) was added at room temperature. The mixture was stirred in a sealed tube for 16 hours at 65° C. The reaction mixture was extracted with saturated NaHCO$_3$ solution and two times with ethyl acetate. The organic layers were washed with water, dried over sodium sulfate and evaporated to dryness. The crude product was purified by flash chromatography on a 50 g silica gel column and eluting with an 0:100 to 100:0 ethyl acetate:heptane gradient. The desired 2-(5-bromo-2-pyridyl)-4,4-dimethyl-1H-imidazol-5-one (785 mg, 84% yield) was obtained as a white solid, MS: m/e=268.3/270.3 (M+H$^+$).

Step 3: 2-(5-Bromo-2-pyridyl)-3,5,5-trimethyl-imidazol-4-one

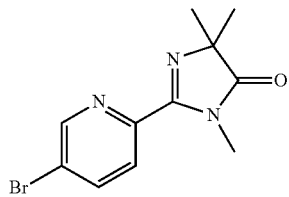 [SMILES: CN1C(=O)C(C)(C)N=C1c1ccc(Br)cn1]

(785 mg, 2.93 mmol) 2-(5-Bromo-2-pyridyl)-4,4-dimethyl-1H-imidazol-5-one (Example 1, step 2) was dissolved in DMF (5 ml) and cooled to 0-5° C. Iodomethane (275 μl, 4.39 mmol, 1.5 equiv.) and NaH (55%) (211 mg, 4.39 mmol, 1.5 equiv.) were added and the mixture was allowed to warm up to room temperature and stirred for 2 hours. The reaction mixture was treated with sat. $NaHCO_3$ solution and extracted twice with ethyl acetate. The organic layers were extracted with water, dried over sodium sulfate and evaporated to dryness. The desired 2-(5-bromo-2-pyridyl)-3,5,5-trimethyl-imidazol-4-one (710 mg, 86% yield) was obtained as a light yellow solid, MS: m/e=282.3/284.3 (M+H$^+$).

Step 4: 2-[5-[2-(3-Fluorophenyl)ethynyl]-2-pyridyl]-3,5,5-trimethyl-imidazol-4-one

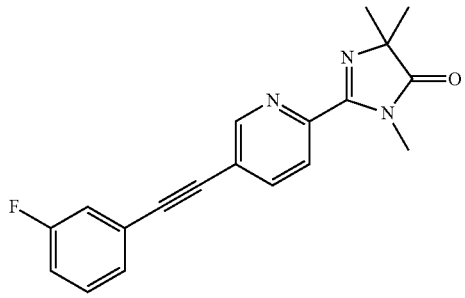 [SMILES: CN1C(=O)C(C)(C)N=C1c1ccc(C#Cc2cccc(F)c2)cn1]

(250 mg, 0.87 mmol) 2-(5-Bromo-2-pyridyl)-3,5,5-trimethyl-imidazol-4-one (Example 1, step 3) was dissolved in DMF (3 ml). 3-Fluorophenylacetylene (213 mg, 1.77 mmol, 2 equiv.), triethylamine (1.24 ml, 8.86 mmol, 10 equiv.), bis-(triphenylphosphine)-palladium(II)dichloride (19 mg, 28 μmol, 0.03 equiv.), triphenylphosphine (14 mg, 56 μmol, 0.06 equiv.) and copper(I)iodide (3 mg, 18 μmol, 0.02 equiv.) were added under nitrogen atmosphere and the mixture was stirred for 3 hours at 80° C. The mixture was evaporated in presence of Isolute® sorbent to dryness. The adsorbed crude material was purified by flash chromatography with a 50 g silica gel column eluting with heptane:ethyl acetate 100:0→30:70. The desired 2-[5-[2-(3-fluorophenyl)ethynyl]-2-pyridyl]-3,5,5-trimethyl-imidazol-4-one (210 mg, 74% yield) was obtained as a light yellow solid, MS: m/e=322.4 (M+H$^+$).

EXAMPLE 2

3,5,5-Trimethyl-2-[5-(2-phenylethynyl)-2-pyridyl]imidazol-4-one

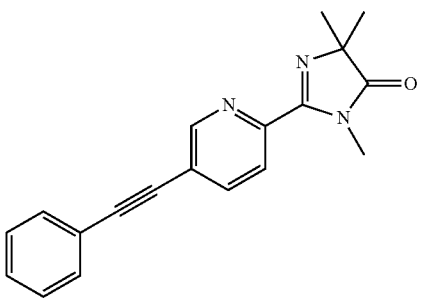 [SMILES: CN1C(=O)C(C)(C)N=C1c1ccc(C#Cc2ccccc2)cn1]

The title compound was obtained as a white solid, MS: m/e=304.4 (M+H$^+$), using chemistry similar to that described in Example 1, step 4 from 2-(5-bromo-2-pyridyl)-3,5,5-trimethyl-imidazol-4-one (Example 1, step 3) and phenylacetylene.

EXAMPLE 3

2-[5-[2-(3-Chlorophenyl)ethynyl]-2-pyridyl]-3,5,5-trimethyl-imidazol-4-one

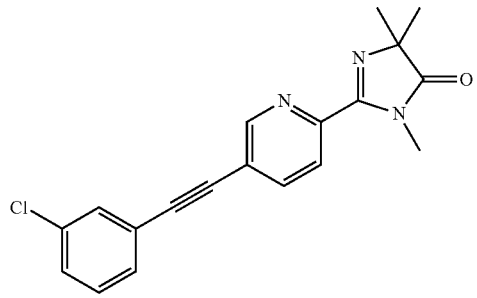 [SMILES: CN1C(=O)C(C)(C)N=C1c1ccc(C#Cc2cccc(Cl)c2)cn1]

The title compound was obtained as a white solid, MS: m/e=338.4/340.4 (M+H$^+$), using chemistry similar to that described in Example 1, step 4 from 2-(5-bromo-2-pyridyl)-3,5,5-trimethyl-imidazol-4-one (Example 1, step 3) and 3-chlorophenylacetylene.

EXAMPLE 4

2-[5-[2-(3-Chlorophenyl)ethynyl]-2-pyrimidyl]-3,5,5-trimethyl-imidazol-4-one

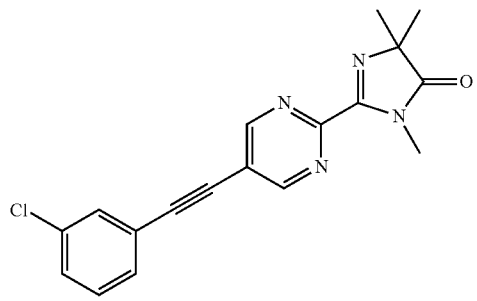 [SMILES: CN1C(=O)C(C)(C)N=C1c1ncc(C#Cc2cccc(Cl)c2)cn1]

Step 1: 5-(3-Chloro-phenylethynyl)-pyrimidine-2-carboxylic acid

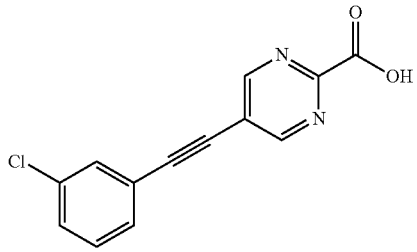 [SMILES: O=C(O)c1ncc(C#Cc2cccc(Cl)c2)cn1]

Bis-(triphenylphosphine)-palladium(II)dichloride (86 mg, 123 μmol, 0.01 equiv.) was dissolved in 12 ml of DMF. (2.5 g, 12.3 mmol) 5-Bromo-pyrimidine-2-carboxylic acid and 3-chlorophenylacetylene (2.02 g, 14.8 mmol, 1.2 equiv.) were added at room temperature. Triethylamine (11 ml, 78.8 mmol, 6.4 equiv.), triphenylphosphine (65 mg, 246 μmol, 0.02 equiv.) and copper(I)iodide (24 mg, 123 μmol, 0.01 equiv.) were added and the mixture was stirred for 2 hours at 80° C. The reaction mixture was cooled to room temperature, diluted with 5 ml of ethyl acetate and 20 ml water. A 2N solution of 2N HCl (20 ml) was added dropwise and the mixture was stirred for 20 minutes at room temperature. The solid was filtered, washed with 10 ml of TBME concentrated in vacuo. The desired 5-(3-chloro-phenyl ethynyl)-pyrimidine-2-carboxylic acid (2.8 g, 88% yield) was obtained as a white solid, MS: m/e=259.4/261.4 (M+H$^+$).

Step 2: N-(2-Amino-1,1-dimethyl-2-oxo-ethyl)-5-[2-(3-chlorophenyl)ethynyl]pyrimidine-2-carboxamide

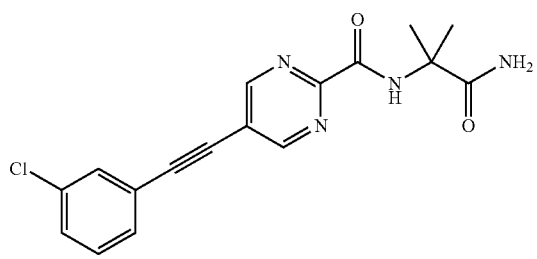 [SMILES: CC(C)(NC(=O)c1ncc(C#Cc2cccc(Cl)c2)cn1)C(N)=O]

The title compound was obtained as a yellow solid, MS: m/e=341.3/343.4 (M+H$^+$), using chemistry similar to that described in Example 1, step 1 from 5-(3-chloro-phenylethynyl)pyrimidine-2-carboxylic acid (Example 4, step 1) and 2-amino-2-methylpropanamide hydrochloride.

Step 3: 2-[5-[2-(3-Chlorophenyl)ethynyl]pyrimidin-2-yl]-4,4-dimethyl-1H-imidazol-5-one

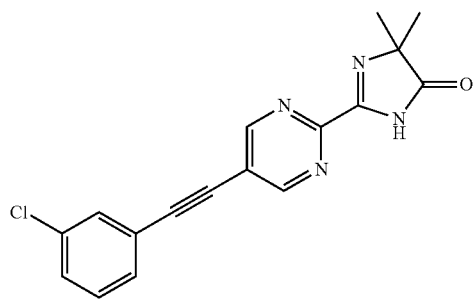 [SMILES: CC1(C)N=C(c2ncc(C#Cc3cccc(Cl)c3)cn2)NC1=O]

The title compound was obtained as a white solid, MS: m/e=325.4/327.4 (M+H$^+$), using chemistry similar to that described in Example 1, step 2 from N-(2-amino-1,1-dimethyl-2-oxoethyl)-5-[2-(3-chlorophenyl)ethynyl]pyrimidine-2-carboxamide (Example 4, step 2).

Step 4: 2-[5-[2-(3-Chlorophenyl)ethynyl]-2-pyrimidyl]-3,5,5-trimethyl-imidazol-4-one

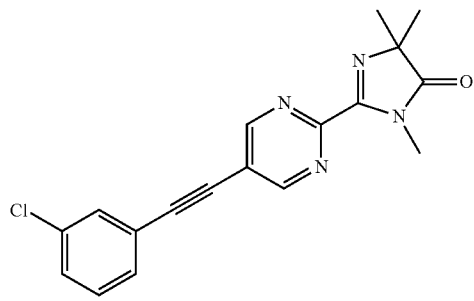 [SMILES: CN1C(=O)C(C)(C)N=C1c1ncc(C#Cc2cccc(Cl)c2)cn1]

The title compound was obtained as a white solid, MS: m/e=339.4/341.3 (M+H$^+$), using chemistry similar to that described in Example 1, step 3 from 2-[5-[2-(3-chlorophenyl)ethynyl]pyrimidin-2-yl]-4,4-dimethyl-1H-imidazol-5-one (Example 4, step 3) and iodomethane.

EXAMPLE 5

3,5,5-Trimethyl-2-[5-(2-phenylethynyl)-2-pyrimidyl]imidazol-4-one

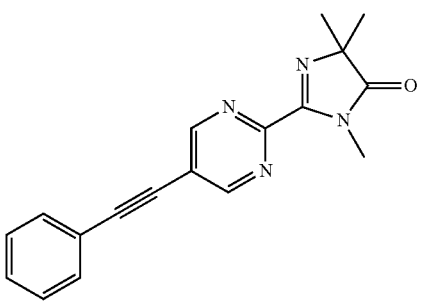 [SMILES: CN1C(=O)C(C)(C)N=C1c1ncc(C#Cc2ccccc2)cn1]

Step 1: 5-(2-Phenylethynyl)pyrimidine-2-carboxylic acid

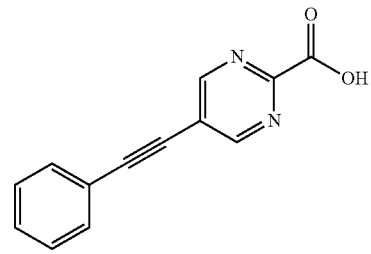 [SMILES: O=C(O)c1ncc(C#Cc2ccccc2)cn1]

The title compound was obtained as a dark brown solid, MS: m/e=222.9 (M−H$^+$), using chemistry similar to that described in Example 4, step 1 from 5-bromo-pyrimidine-2-carboxylic acid and phenylacetylene.

Step 2: N-(2-Amino-1,1-dimethyl-2-oxo-ethyl)-5-(2-phenylethynyl)pyrimidine-2-carboxamide

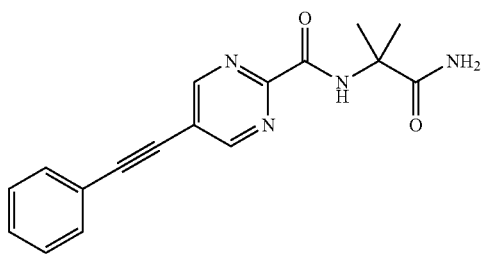 [SMILES: CC(C)(NC(=O)c1ncc(C#Cc2ccccc2)cn1)C(N)=O]

The title compound was obtained as a yellow oil, MS: m/e=309.4 (M+H$^+$), using chemistry similar to that described in Example 1, step 1 from 5-(2-phenylethynyl)pyrimidine-2-carboxylic acid (Example 5, step 1) and 2-amino-2-methylpropanamide hydrochloride.

Step 3: 4,4-Dimethyl-2-[5-(2-phenylethynyl)pyrimidin-2-yl]-1H-imidazol-5-one

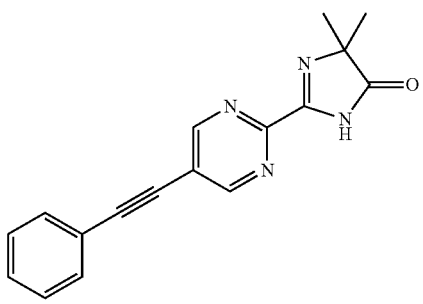 [SMILES: CC1(C)N=C(c2ncc(C#Cc3ccccc3)cn2)NC1=O]

The title compound was obtained as a yellow solid, MS: m/e=291.4 (M+H$^+$), using chemistry similar to that described in Example 1, step 2 from N-(2-amino-1,1-dimethyl-2-oxo-ethyl)-5-(2-phenylethynyl)pyrimidine-2-carboxamide (Example 5, step 2).

Step 4: 3,5,5-Trimethyl-2-[5-(2-phenylethynyl)pyrimidin-2-yl]imidazol-4-one

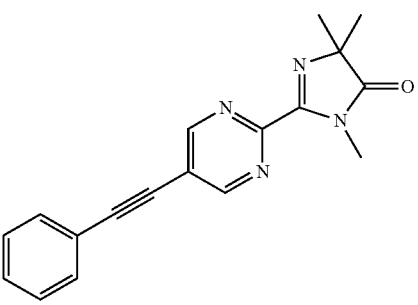 [SMILES: CN1C(=O)C(C)(C)N=C1c1ncc(C#Cc2ccccc2)cn1]

The title compound was obtained as a yellow solid, MS: m/e=305.4 (M+H$^+$), using chemistry similar to that described in Example 1, step 3 from 4,4-dimethyl-2-[5-(2-phenylethynyl)pyrimidin-2-yl]-1H-imidazol-5-one (Example 5, step 3) and iodomethane.

EXAMPLE 6

2-[5-[2-(3-Fluorophenyl)ethynyl]-2-pyrimidyl]-3,5,5-trimethyl-imidazol-4-one

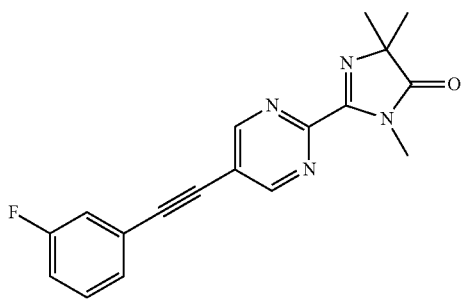 [SMILES: CN1C(=O)C(C)(C)N=C1c1ncc(C#Cc2cccc(F)c2)cn1]

Step 1: 5-(3-Fluoro-phenylethynyl)-pyrimidine-2-carboxylic acid

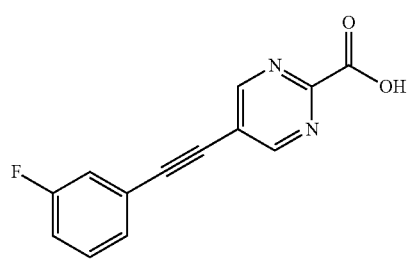 [SMILES: O=C(O)c1ncc(C#Cc2cccc(F)c2)cn1]

The title compound was obtained using chemistry similar to that described in Example 4, step 1 from 5-bromo-pyrimidine-2-carboxylic acid and 3-fluorophenylacetylene.

Step 2: N-(2-Amino-1,1-dimethyl-2-oxo-ethyl)-5-[2-(3-fluorophenyl)ethynyl]pyrimidine-2-carboxamide

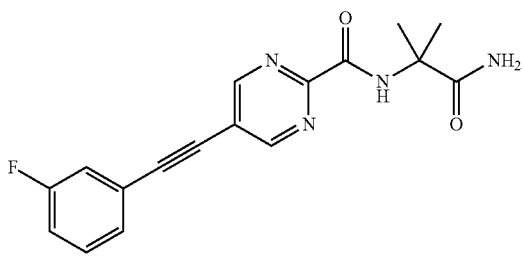 [SMILES: CC(C)(NC(=O)c1ncc(C#Cc2cccc(F)c2)cn1)C(N)=O]

The title compound was obtained as a yellow solid, MS: m/e=327.4 (M+H⁺), using chemistry similar to that described in Example 1, step 1 from 5-(3-fluoro-phenylethynyl)-pyrimidine-2-carboxylic acid (Example 6, step 1) and 2-amino-2-methylpropanamide hydrochloride.

Step 3: 2-[5-[2-(3-Fluorophenyl)ethynyl]pyrimidin-2-yl]-4,4-dimethyl-1H-imidazol-5-one

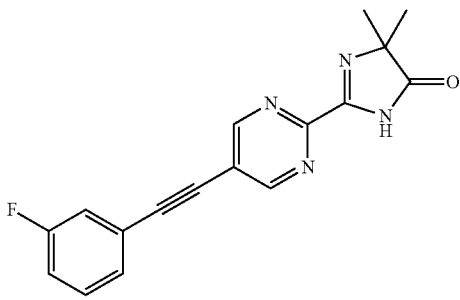 [SMILES: CC1(C)N=C(c2ncc(C#Cc3cccc(F)c3)cn2)NC1=O]

The title compound was obtained as a yellow solid, MS: m/e=309.3 (M+H⁺), using chemistry similar to that described in Example 1, step 2 from N-(2-amino-1,1-dimethyl-2-oxo-ethyl)-5-[2-(3-fluorophenyl)ethynyl]pyrimidine-2-carboxamide (Example 6, step 2).

Step 4: 2-[5-[2-(3-Fluorophenyl)ethynyl]-2-pyrimidyl]-3,5,5-trimethyl-imidazol-4-one

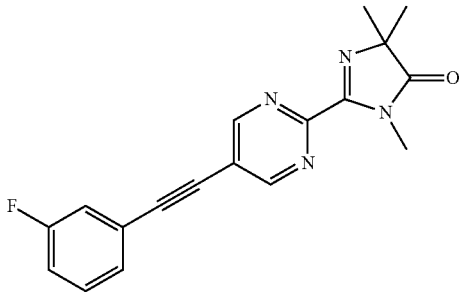 [SMILES: CN1C(=O)C(C)(C)N=C1c1ncc(C#Cc2cccc(F)c2)cn1]

The title compound was obtained as an orange solid, MS: m/e=323.4 (M+H⁺), using chemistry similar to that described in Example 1, step 3 from 2-[5-[2-(3-fluorophenyl)ethynyl]pyrimidin-2-yl]-4,4-dimethyl-1H-imidazol-5-one (Example 6, step 3) and iodomethane.

The invention claimed is:

1. A compound of formula I

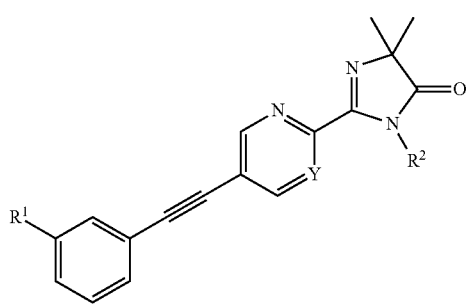

wherein

Y is CH;

R¹ is hydrogen, fluoro or chloro; and

R² is hydrogen or lower alkyl;

or a pharmaceutically acceptable acid addition salt thereof.

2. A compound of formula I according to claim 1, selected from the group consisting of 2-[5-[2-(3-Fluorophenyl)ethynyl]-2-pyridyl]-3,5,5-trimethyl-imidazol-4-one 3,5,5-Trimethyl-2-[5-(2-phenylethynyl)-2-pyridyl]imidazol-4-one and 2-[5-[2-(3-Chlorophenyl)ethynyl]-2-pyridyl]-3,5,5-trimethyl-imidazol-4-one

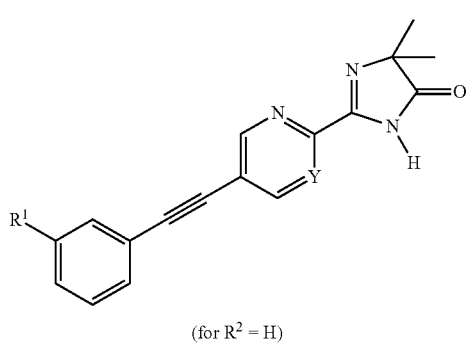

(for R² = H)

and, if desired, alkylating the compound obtained to form a compound of formula

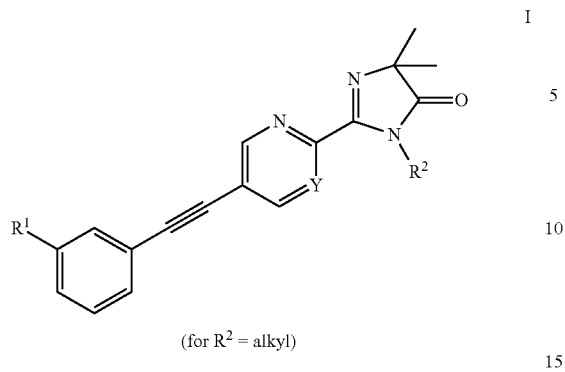
(for R² = alkyl)
wherein the substituents are as described in claim 1.
3. A pharmaceutical composition comprising a compound of formula I according to claim 1 and a therapeutically active carrier.
* * * * *